(12) United States Patent
Scates et al.

(10) Patent No.: US 9,193,657 B2
(45) Date of Patent: Nov. 24, 2015

(54) CATALYST STABILITY IN CARBONYLATION PROCESSES

(75) Inventors: Mark O. Scates, Houston, TX (US);
Ronald D. Shaver, Houston, TX (US);
Gregory Blanchard, Manvel, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/588,596

(22) Filed: Aug. 17, 2012

(65) Prior Publication Data

US 2014/0051885 A1 Feb. 20, 2014

(51) Int. Cl.
*C07C 51/12* (2006.01)

(52) U.S. Cl.
CPC ...................... *C07C 51/12* (2013.01)

(58) Field of Classification Search
CPC ........................................................ C07C 51/12
USPC .................. 562/519, 517, 891, 890
See application file for complete search history.

(56) References Cited

U.S. PATENT DOCUMENTS

| | | | |
|---|---|---|---|
| 3,769,329 A | 10/1973 | Knox et al. | |
| 4,098,339 A * | 7/1978 | Weisz et al. | 166/305.1 |
| 4,255,591 A * | 3/1981 | Makin et al. | 562/517 |
| 4,994,608 A | 2/1991 | Torrence et al. | |
| 5,001,259 A | 3/1991 | Smith et al. | |
| 5,026,908 A | 6/1991 | Smith et al. | |
| 5,144,068 A | 9/1992 | Smith et al. | |
| 5,237,097 A | 8/1993 | Smith et al. | |
| 5,334,755 A | 8/1994 | Yoneda et al. | |
| 5,683,492 A | 11/1997 | Hesse et al. | |
| 5,756,828 A * | 5/1998 | Arnoldy et al. | 560/207 |
| 5,840,969 A * | 11/1998 | Joensen | 562/519 |
| 6,255,527 B1 | 7/2001 | Muskett | |
| 7,476,761 B2 | 1/2009 | Kojima | |
| 7,619,113 B2 * | 11/2009 | Powell | 562/519 |
| 2008/0293996 A1 | 11/2008 | Evans et al. | |
| 2011/0009665 A1 * | 1/2011 | Scates | 562/519 |
| 2011/0077428 A1 * | 3/2011 | Zinobile et al. | 562/608 |
| 2012/0083623 A1 | 4/2012 | Hokkanen et al. | |

OTHER PUBLICATIONS

International Search Report and Written Opinion for PCT/US2013/054913 mailed Jan. 22, 2014.

* cited by examiner

*Primary Examiner* — Paul A Zucker
*Assistant Examiner* — Mark Luderer

(57) ABSTRACT

A method for stabilizing a carbonylation catalyst with carbon monoxide recovered from a gaseous stream derived from a carbonylation reaction. The carbon monoxide enriched stream is fed downstream of the carbonylation reactor, preferably to a flasher or light ends column, to enhance catalyst stability throughout the process.

25 Claims, 2 Drawing Sheets

CATALYST STABILITY IN CARBONYLATION PROCESSES

FIELD OF THE INVENTION

The present invention relates to carbonylation processes for forming carboxylic acids and, in particular, to enhancing catalyst stability in such processes using recovered carbon monoxide.

BACKGROUND OF THE INVENTION

A widely used and successful commercial process for synthesizing acetic acid involves the catalyzed carbonylation of methanol with carbon monoxide. The homogenous catalysts contain rhodium and/or iridium and a halogen promoter, typically methyl iodide. The reaction is conducted by continuously bubbling carbon monoxide through a liquid reaction medium containing the homogenous catalyst. In addition to the catalyst, the reaction medium also comprises methanol, methyl acetate, water, and methyl iodide. The carbonylation product is withdrawn from the reactor and separated in a flasher into a catalyst-containing solution, which is typically recycled to the reactor, and a vapor product stream. Further purification and separation of the vapor product stream yields the desired acetic acid. The homogenous catalyst, whether in the reactor, flasher, or being transferred between the reactor and flasher, should remain relatively stable to prevent loss of catalytic function through, for example, precipitation.

As developed, the rhodium-catalyzed carbonylation process employed a water concentration of over 14 wt. % based on the weight of the total reaction medium, as described in U.S. Pat. No. 3,769,329. Water enhances the reaction rate at the expense of purification capacity. Also, a substantial amount of energy is required to remove water. To reduce the need for water removal, "low water" processes were subsequently developed. Examples of these low water processes include those described in U.S. Pat. Nos. 5,001,259; 5,026,908; and 5,144,068, which are hereby incorporated by reference. These low water carbonylation processes maintain catalyst stability and increase productivity at high levels by maintaining an iodide salt in the reaction medium. Even under these conditions, however, catalyst instability and catalyst precipitation may be problematic. U.S. Pat. No. 4,994,608, the entirety of which is incorporated herein by reference, relates to catalyst stabilization via an increase in hydrogen partial pressure in the reaction medium. In addition, increases of carbon monoxide partial pressure may also help stabilize the catalyst in the reaction medium.

Carbon monoxide, as a raw material, may contain hydrogen, which is a building block to heavy impurities. These heavy impurities require further purification and separation reducing operating efficiencies. In a typical continuous carbonylation process, the partial pressures of hydrogen and carbon monoxide are controlled by venting of the vapor-filled portion of the carbonylation reactor. The venting prevents the buildup of gases, e.g., hydrogen, carbon dioxide and methane, within the reactor. The buildup of these gases may lead to undesirable side reactions that reduce production yields and introduce impurities into the product acetic acid. Unreacted carbon monoxide is a major component of the vented gases, commonly comprising about 50 to 80 mol. % of the total vented gases. Thus, the venting of these gases results in a substantial loss of carbon monoxide reactant, which decreases overall carbon monoxide efficiency.

Readily condensable gases from the reactor are typically condensed and the resultant liquids, such as iodides and esters, are recovered and returned to the process. Non-condensable gases, such as carbon monoxide, may be purged from the system or recovered. U.S. Pat. No. 4,255,591, for example, describes recovering carbon monoxide by passing the reactor vent gas through a hollow fiber semi-permeable membrane to produce a non-permeated portion enriched with carbon monoxide. Similarly, U.S. Pat. No. 5,334,755 describes separating a gas portion of carbon monoxide and returning it to the reactor. U.S. Pat. No. 5,683,492 describes recovering carbon monoxide from a purge gas stream that is passed through a pressure swing adsorption process. The recovered gas fraction, enriched with carbon monoxide, is returned to the reactor. However, returning carbon monoxide to the reactor requires compressing the recovered gas fraction at high energy expense to a pressure that is equal to or greater than the pressure of the fresh carbon monoxide that is fed to the reactor.

Other efforts have sought to regulate the amount of carbon monoxide fed to the reactor. U.S. Pat. No. 7,476,761, for example, describes a control process for monitoring carbon monoxide concentrations to maintain catalyst stability. U.S. Pat. No. 6,255,527 describes a method of controlling the flow of carbon monoxide to prevent the flow of carbon monoxide from exceeding a calculated point. Even though the amount of carbon monoxide fed to the reactor is regulated in these cases, the excess carbon monoxide is either purged or fed back to the reactor.

In addition to maintaining catalyst stability in the reactor, it is also desirable to maintain catalyst stability downstream of the reactor, e.g., in the flasher, separation zone, and in the connecting pipes. Fresh carbon monoxide may be added downstream of the reactor, but this carbon monoxide generally carries over with the vapor stream from the flasher and is purged. U.S. Pat. No. 5,237,097 discloses an organic compound that is reacted with carbon monoxide in the presence of a Group VIII metal-containing catalyst. The liquid carbonylation product solution of this reaction is conveyed to a separation zone maintained at a lower total pressure than is the pressure in the reaction zone. Simultaneously with the conveyance of the liquid product solution to the separation zone is the introduction therein of a carbon monoxide-containing gaseous stream, the carbon monoxide therein contributing a partial pressure of up to 30 psia of the total pressure in the separation zone. No provisions are provided in U.S. Pat. No. 5,237,097 concerning the carbon monoxide introduced to the separation zone and the carbon monoxide would be subsequently purged when purifying the flashed portion of the liquid product solution. US Pub. No. 2008/0293996 describes using a portion of the non-condensable gases that contain carbon monoxide from the reactor to stabilize the catalyst in the bottom of the flasher. However, the carbon monoxide that is fed downstream of the reactor is purged after scrubbing with methanol.

The need remains for improved carbonylation processes with increased catalyst stability while maximizing reaction efficiencies.

SUMMARY OF THE INVENTION

The present invention is directed to carbonylation processes with improved catalyst stability. In a first embodiment, the invention is to a method for enhancing catalyst stability in an acetic acid production process comprising the steps of reacting carbon monoxide with at least one reactant selected from the group consisting of methanol, methyl acetate, methyl formate, dimethyl ether and mixtures thereof in a reactor containing a reaction medium to produce a reaction product comprising acetic acid. The reaction product is separated into a crude acetic acid stream and a catalyst-containing solution. The crude acetic acid stream is distilled to yield a product stream, preferably a product side stream, comprising acetic acid and an overhead vapor stream comprising at least a portion of the unreacted carbon monoxide. The overhead vapor stream is condensed and directing to a decanter. Uncondensed gases, such as carbon monoxide, are withdrawn from the decanter, and introduced downstream of the reactor for improved catalyst stability.

In a second embodiment, the invention is to a method for enhancing catalyst stability in an acetic acid production process comprising the steps of reacting carbon monoxide with at least one reactant selected from the group consisting of methanol, methyl acetate, methyl formate, dimethyl ether and mixtures thereof in a reactor containing a reaction medium to produce a reaction product comprising acetic acid; venting a gaseous stream from the reactor; recovering a first carbon monoxide enriched stream from the vented gases, and introducing a portion of the first carbon monoxide enriched stream downstream of the reactor.

In a third embodiment, the invention is to a method for enhancing catalyst stability in an acetic acid, acetic anhydride co-production process, comprising the steps of: reacting carbon monoxide with at least one reactant selected from the group consisting of methanol, methyl acetate, methyl formate, dimethyl ether and mixtures thereof in a reactor containing a reaction medium to produce a reaction product comprising acetic acid and acetic anhydride; venting a gaseous stream from the reactor; and introducing at least a portion of the vented gaseous stream downstream of the reactor, e.g., to a product stream and/or to a unit in a separation scheme employed in the process such as a falling film evaporator.

BRIEF DESCRIPTION OF THE DRAWINGS

The invention is described in detail below with reference to the appended drawings, wherein like numerals designate similar parts.

DETAILED DESCRIPTION OF THE INVENTION

Figure 1:
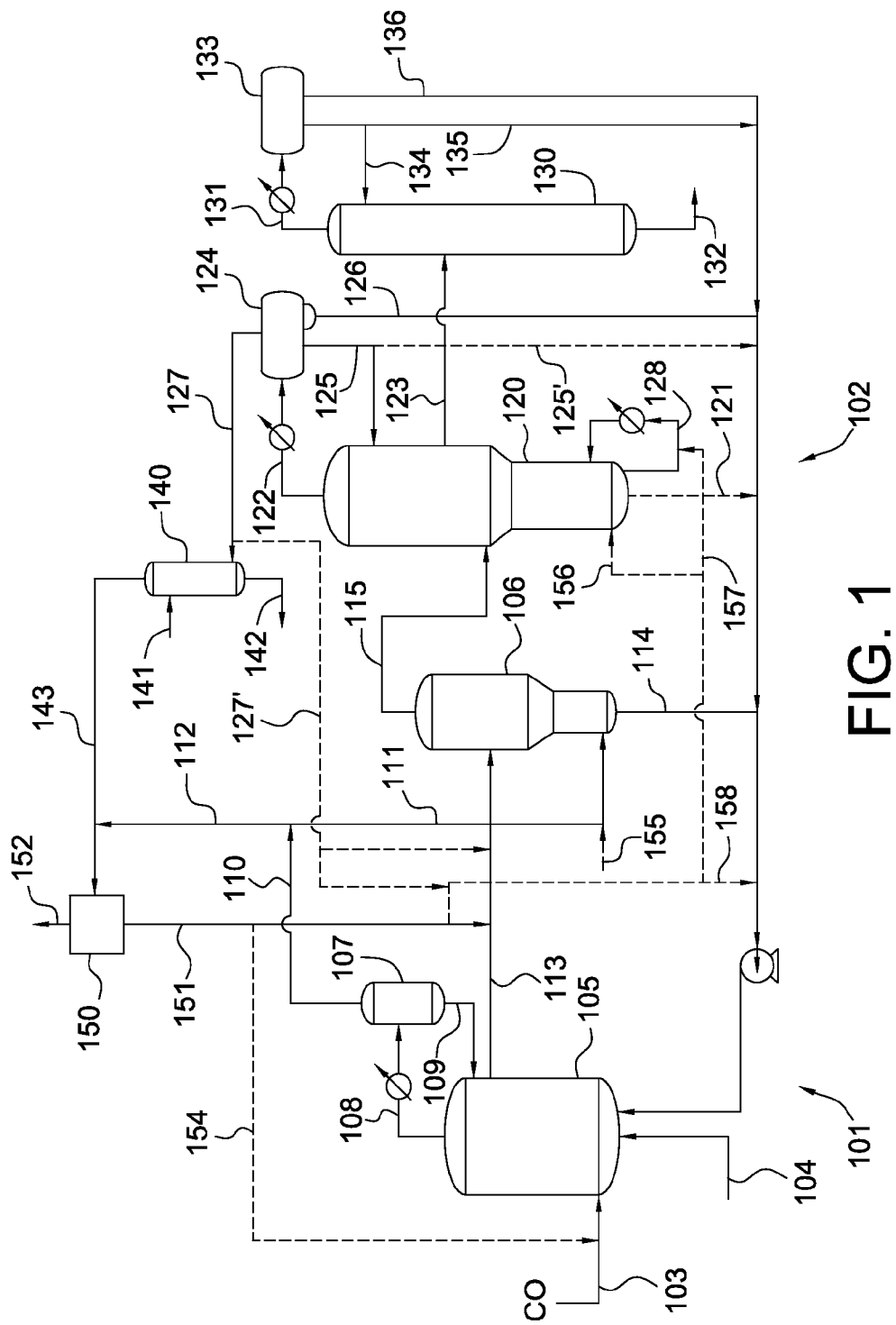
FIG. 1 is a schematic diagram of a carbonylation process having a carbon monoxide recovery unit in accordance with one embodiment of the present invention.

In general, the present invention relates to processes for maintaining catalyst stability, in particular in regions downstream of a carbonylation reactor, when producing acetic acid through a carbonylation process. In the carbonylation reactor, the partial pressure of carbon monoxide desirably may be increased to improve catalyst stabilization. This results in increased carbon monoxide venting from the reactor and associated purification section. The present invention involves recovering carbon monoxide, directly or indirectly, from a gaseous stream that is vented from the reactor or purification section, preferably at increased vent rates, and using the recovered carbon monoxide to stabilize the carbonylation catalyst, preferably in locations downstream of the reactor. In contrast to prior catalyst stabilization systems, in the present invention the carbon monoxide is recovered from either or both the reactor and/or the purification section and is reintroduced downstream of the reactor. Thus, in preferred embodiments, carbon monoxide is recovered from the reactor vent stream and/or from a vent stream derived from the purification section, e.g., from the overhead of a light ends distillation column and ideally from a decanter of the light ends distillation column. The recovered carbon monoxide is introduced downstream of the reactor to enhance catalyst stability and reduce catalyst precipitation.

The recovered carbon monoxide is introduced at any location downstream of the reactor that contains the catalyst or that is upstream of a location that contains the catalyst. Since the carbon monoxide is introduced downstream of the reactor, the carbon monoxide preferably passes into the purification section where the carbon monoxide is subsequently recovered. In one embodiment, prior to introducing the carbon monoxide downstream of the reactor, the recovered carbon monoxide stream is treated to remove impurities and enrich carbon monoxide content. In a continuous process, introduced carbon monoxide that is recycled from vent streams may beneficially stabilize the catalyst without the need for fresh carbon monoxide. Thus, the present invention advantageously enhances catalyst stability throughout the process, including in the reactor, by allowing for increased carbon monoxide feed rates and partial pressures in the reactor as well as the purification section.

In one embodiment, the vent rate from the reactor is increased to accommodate the increased gas flow in the reactor that is desired to operate the carbonylation reaction at increased carbon monoxide partial pressures. Once withdrawn from the reactor, the carbon monoxide may be recovered from the reactor vent gas and/or from a vent stream derived from the purification section. In optional embodiments, the flow rate of the gaseous vent stream optionally is from 0.1 to 10%, e.g., from 0.2 to 8%, of the flow rate of carbon monoxide fed to the reactor.

As a result of the increased vent rate, an increased amount of impurities, e.g., hydrogen, carbon dioxide and methane, are removed from the reactor in the vent gas. Without being bound by theory, operating at increased carbon monoxide flow rates and at increased vent rates may result in a more pure acetic acid product, even when lower grade carbon monoxide is employed, when compared to conventional carbon monoxide flow rates. As a result, the ability to remove an increased amount of impurities from the reactor without losing a significant amount of carbon monoxide may beneficially simplify the subsequent purification section. In particular, because the carbonylation reaction product may comprise a lower amount of impurities, the size of the columns for removing aldehydes, and heavier acids, such as propionic acid, may be reduced and/or one or more separation columns may be eliminated.

Figure 2:
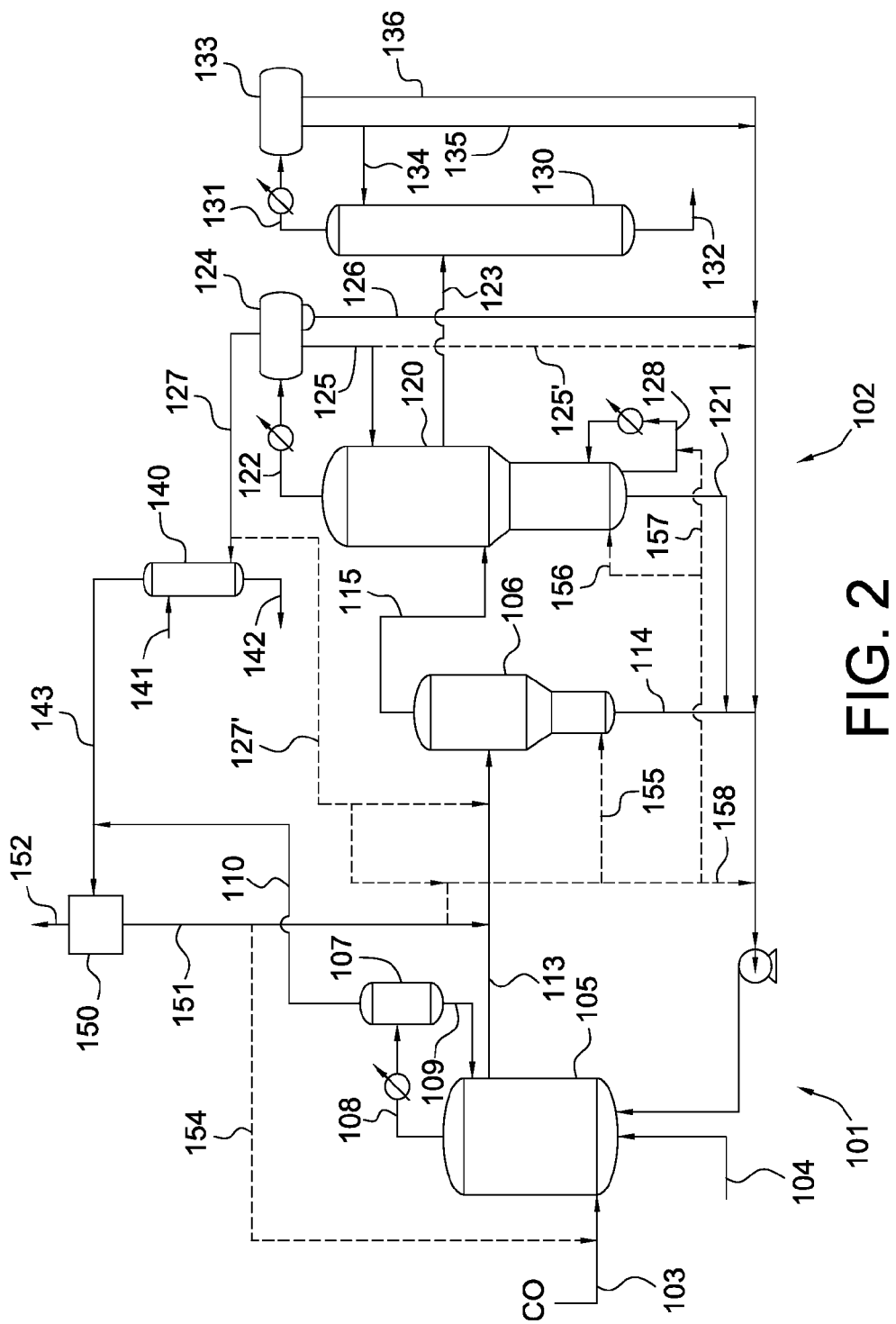
FIG. 2 is a schematic diagram of a carbonylation process having a carbon monoxide recovery unit in accordance with another embodiment of the present invention.

The present invention may be applied to any suitable carbonylation process, but preferably is employed in a methanol carbonylation process. Exemplary carbonylation processes that may be used with embodiments of the present invention include those described in U.S. Pat. Nos. 7,223,886; 7,005,541; 6,657,078; 6,339,171; 5,731,252; 5,144,068; 5,026,908; 5,001,259; and 4,994,608, and U.S. Pub. Nos. 2008/0287706; 2008/0293966; 2009/0107833; and 2009/0270651, all of which are hereby incorporated by reference. The exemplary carbonylation systems depicted herein may also include further systems and components described in those patents that may be used with embodiments of the present invention. It should be understood that the carbonylation system shown in FIGS. 1 and 2 are merely exemplary and that it is within the scope of the present invention to use other components. The carbonylation processes of the present invention comprise a carbonylation section and a purification section. Any suitable carbonylation or purification section may be used in combination with any of the embodiments of the present invention.

Exemplary carbonylation systems are shown in FIGS. 1 and 2. Each system includes a carbonylation section 101 and a purification section 102. Carbonylation section 101 comprises a carbon monoxide feed stream 103, a reactant feed stream 104, a reactor 105, a flasher 106, and a recovery unit 107. Carbon monoxide, at least a portion of which preferably comprises fresh carbon monoxide, is fed via feed stream 103 to a lower portion of reactor 105. Reactant feed stream 104 comprises at least one reactant selected from the group consisting of methanol, methanol derivatives, such as methyl acetate, methyl formate, dimethyl ether, and mixtures thereof. In preferred embodiments, reactant feed stream 104 supplies methanol and optionally methyl acetate to reactor 105. The concentration of methyl acetate in the reaction medium preferably is in the range from 0.5 wt. % to 35 wt. %, e.g., from 0.5 wt. % to 10 wt. %, or from 0.5 wt. % to 5 wt. %, based on the total weight of the reaction medium. Optionally, reactant feed stream 104 may be connected to one or more vessels (not shown) that store fresh reactants for the carbonylation process.

One or more process streams from carbonylation section 101 may be recycled to reactor 105. In some embodiments, recycle streams comprising the reaction medium components, e.g., residual/entrained catalyst, methyl iodide, water, acetic acid, or mixtures thereof, are recycled to the reactor. Also, one or more process streams from purification section 102 may be fed to reactor 105. Preferably, multiple process streams are recycled and fed, directly or indirectly, in combination or separately, to reactor 105. As used herein, the term "fed directly" refers to utilizing a stream that has not been compositionally modified, and the term "fed indirectly" refers to utilizing a modified stream, for example, a stream that has had components added thereto or removed therefrom. The recycled process streams are preferably introduced in the lower portion of reactor 105.

Carbon monoxide feed stream 103 may comprise substantially pure carbon monoxide having small amounts of inerts and impurities, e.g., less than 1 mol. %, e.g., less than 0.5 mol. %. The inerts and impurities may include, for example, carbon dioxide, methane, nitrogen, hydrogen, noble gases, water and $C_1$ to $C_4$ paraffinic hydrocarbons.

As discussed above, the increased vent rates contemplated by the present invention provide the ability to remove an increased amount of inerts and impurities from carbonylation reactor 105. Accordingly, the increased vent rates advantageously may allow for the use of lower, less expensive, grades of carbon monoxide. As used herein, lower grades of carbon monoxide refers to any carbon monoxide stream having more impurities than substantially pure carbon monoxide, as described above. Low grade carbon monoxide feed streams may comprise, for example, at least 0.5 mol. % hydrogen, at least 0.5 mol. % methane, and/or at least 0.5 mol. % nitrogen. The hydrogen content in the reactor is preferably kept low, e.g., less than 1 bar partial pressure of hydrogen or less than 0.5 bar partial pressure of hydrogen, as its presence may result in the formation of hydrogenation byproducts. In terms of ranges, the hydrogen partial pressure in reactor 105 may be from 0.1 to 4 bar, e.g., from 0.1 to 2 bar, or from 0.1 to 0.5 bar. The carbon monoxide partial pressure in reactor 105 preferably is greater than 2 bar, e.g., greater than 5 bar, or greater than 7 bar. In general, the carbon monoxide partial pressure in the reactor may be less than 30 bar, e.g., less than 20 bar or less than 15 bar. In some embodiments, there is no upper limit on partial pressure of carbon monoxide and it may be preferable to operate reactor 105 at the highest carbon monoxide partial pressure possible to maintain catalyst stability.

In one aspect of the present invention, carbon monoxide may be obtained by a steam reforming process in which a hydrocarbon feed stock, such as natural gas, refinery gas, liquefied gas or naphtha, or a biomass source, is treated with water vapor at elevated temperatures in the presence of a catalyst and is converted into synthesis gas (syngas), which comprises hydrogen and carbon monoxide. The syngas may be separated after cooling such that the carbon dioxide and water vapor still contained therein are removed by scrubbing with a suitable material.

In some embodiments of the invention, methanol is reacted with carbon monoxide in a homogeneous catalytic reaction system comprising a reaction solvent, methanol and/or methanol derivatives, a Group VIII catalyst, at least a finite concentration of water and optionally an iodide salt.

Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]^-$ anion, as is well known in the art. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate or a mixture thereof. The optional iodide catalyst stabilizer may be added as a non-iodide salt that will generate an iodide salt. The iodide catalyst stabilizer may be introduced directly into the reaction system. Alternatively, the iodide salt may be generated in situ since under the operating conditions of the reaction system, a wide range of non-iodide salt precursors will react with methyl iodide or hydrogen iodide to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is used, the iridium catalyst may comprise any iridium-containing compound that is soluble in the reaction medium. The iridium catalyst may be added to the reaction medium for the carbonylation reaction in any suitable form that dissolves in the reaction medium or is convertible to a soluble form. Examples of suitable iridium-containing compounds that may be added to the reaction medium include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)^-_2Br_2]^-H+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$ and hexachloroiridic acid $[H_2IrCl_6]$. Chloride-free complexes of iridium such as acetates, oxalates, and acetoacetates are usually employed as starting materials. The iridium catalyst concentration in the reaction medium generally ranges from 100 to 6000 wppm. The carbonylation of methanol using iridium catalyst is well known and is generally described in U.S. Pat. Nos. 5,942,460; 5,932,764; 5,883,295; 5,877,348; 5,877,347; and 5,696,284, which are hereby incorporated by reference.

Other promoters and co-promoters may be used as part of the catalytic system of the present invention, as described in EP0849248, the entirety of which is hereby incorporated by reference. Suitable promoters include those selected from ruthenium, osmium, tungsten, rhenium, zinc, cadmium, indium, gallium, mercury, nickel, platinum, vanadium, titanium, copper, aluminum, tin and antimony, and are more preferably selected from ruthenium and osmium. Specific co-promoters are described in U.S. Pat. No. 6,627,770, which is incorporated herein by reference.

The promoter(s) may be present in an effective amount up to the limit of its solubility in the reaction medium and/or any liquid process streams recycled to the reactor from the purification train. When used, the promoter is suitably present in the reaction medium at a molar ratio of promoter to metal catalyst of 0.5:1 to 15:1, preferably 2:1 to 10:1, more preferably 2:1 to 7.5:1. A suitable promoter concentration is 400 to 5000 wppm.

A halogen co-catalyst/promoter is generally used in combination with the Group VIII metal catalyst component. Methyl iodide is a preferred halogen promoter. Preferably, the concentration of halogen promoter in the reaction medium ranges from 1 wt. % to 50 wt. %, and preferably from 2 wt. % to 30 wt. %.

The halogen promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Water may be formed in situ in the reaction medium, for example, by the esterification reaction between methanol reactant and acetic acid product. In some embodiments, water is introduced to reactor 105 together with or separately from other components of the reaction medium. Water may be separated from the other components of reaction product withdrawn from reactor 105 and may be recycled in controlled amounts to maintain the required concentration of water in the reaction medium. Preferably for carbonylating methanol, the concentration of water is maintained in the reaction medium in an amount from 0.1 wt. % to 16 wt. %, e.g., from 1 wt. % to 14 wt. %, or from 1 wt. % to 3 wt. % of the total weight of the reaction product. In some embodiments, for example when co-producing acetic anhydride and acetic acid, the carbonylation reaction medium may be anhydrous. Without being bound by theory, carbonylation catalysts tend to have lower stability under low water conditions, e.g., less than 2 wt. %, less than 1 wt. % or in anhydrous conditions.

In accordance with a preferred embodiment of the present invention, the desired reaction rates are obtained even at low water concentrations by maintaining, in the reaction medium, an ester of the desired carboxylic acid and an alcohol, desirably the primary alcohol used in the carbonylation process, and an additional iodide ion that is over and above the iodide ion that is present as hydrogen iodide. An example of a preferred ester is methyl acetate. The additional iodide ion is desirably an iodide salt, with lithium iodide being preferred. It has been found, as described in U.S. Pat. No. 5,001,259, that under low water concentrations, methyl acetate and lithium iodide act as rate promoters when relatively high concentrations of each of these components are present and that the promotion is higher when both of these components are present simultaneously. The absolute concentration of iodide ion content does not limit the usefulness of the present invention.

In reactor 105 the reaction medium is maintained, preferably automatically, at a predetermined level. This predetermined level may remain substantially constant during normal operation. Methanol, carbon monoxide, and sufficient water may be continuously introduced into reactor 105 as needed to maintain, in preferred embodiments, at least a finite concentration of water in the reaction medium. In some embodiments, carbon monoxide may be bubbled through the reaction medium. Carbon monoxide feed 103 is continuously introduced at a rate sufficient to maintain the total reactor pressure.

In one embodiment, the temperature of reactor 105 may be controlled using heat exchangers in a pump-around loop (not shown).

Acetic acid is typically manufactured in a liquid phase reaction at a temperature from about 160° C. to about 220° C. and a total pressure from about 20 bar to about 50 bar. In some embodiments of the invention, reactor 105 is operated at a temperature from 150° C. to 250° C., e.g., from 155° C. to 235° C., or from 160° C. to 220° C.

In one embodiment, gaseous stream 108 is vented from reactor 105 to prevent the buildup of gaseous by-products and to maintain a carbon monoxide partial pressure at a given total reactor pressure. Specifically, in continuous carbonylation processes, the vapor-filled headspace portion of reactor 105 is preferably vented to prevent the buildup of hydrogen, carbon dioxide and methane and other gases within the reactor. In venting these undesirable gases, however, unreacted carbon monoxide is also vented. Increasing the vent rate of gaseous stream 108 leads to carbon monoxide loss. By directing carbon monoxide that is recovered from gaseous stream 108 downstream of the reactor for catalyst stabilization, embodiments of the present invention beneficially reduce carbon monoxide losses via vented gaseous stream 108 while increasing catalyst stability in the reactor and purification system.

As shown, gaseous stream 108 may be scrubbed with acetic acid and/or methanol (not shown) in recovery unit 107 to recover readily condensable components, such as methyl acetate, and/or methyl iodide. The recovered condensable components may be returned to the reactor 105 via stream 109. Gaseous stream 110 comprises carbon monoxide preferably in an amount from 40 to 95 mol. %, e.g., from 50 to 90 mol. % or from 55 to 80 mol. %. The remaining portion of stream 110 may comprise uncondensed gases, such as carbon dioxide, hydrogen, nitrogen, light hydrocarbons (e.g., methane, ethane), alkyl halides, and mixtures thereof. As shown in FIG. 1, gaseous stream 110 may be split into two aliquot portions. One portion may be fed via line 111 to the base of flasher 106 where the carbon monoxide therein may be used to enhance the stability of any catalyst contained therein. As shown in FIG. 1, the remaining portion may be fed via line 112 to carbon monoxide recovery unit 150. In one embodiment, the flow rate ratio of line 111 to 112 is from 10:1 to 1:10, e.g., from 1:5 to 5:1 or from 2:1 to 1:2. The portion of gaseous stream 110 fed to the flasher 106 via line 111 may pass with the vapor portion (stream 115) from flasher 106 and the uncondensed gases, preferably comprising carbon monoxide, may be later recovered and fed to carbon monoxide recovery unit 150 as described below. Thus, some embodiments of the present invention advantageously involve recovering carbon monoxide that would otherwise be vented, and introduces the recovered carbon monoxide downstream of the reactor to enhance catalyst stabilization downstream of the reactor.

In another embodiment, gaseous stream 110 is not split, but instead the entire portion is fed to carbon monoxide recovery unit 150 as shown in FIG. 2. Removing impurities from gaseous stream 110 may reduce side reactions involving those impurities and improve purification efficiencies. Also, the vapor load on light ends column 120 may be advantageously reduced. In another embodiment, not shown, gaseous stream 110 is not split, but instead the entire portion is fed to the flasher 106 and otherwise is substantially as shown and described with reference to FIG. 1.

Although one vent scrubber 140 is shown in FIGS. 1 and 2, there may be one or more vent scrubbers for each vent stream. Optionally, recovery unit 107 and vent scrubber 140 may be used in combination.

Introducing carbon monoxide downstream of the reactor leads to an increased vapor load on light ends column 120, and thus it may be beneficial to remove any inerts and impurities from gaseous stream 110 prior to introducing it downstream of the reactor. In one embodiment, splitting the gaseous stream 110 in FIG. 1, into two streams in lines 111 and 112 may advantageously decrease the vapor load on light ends column 120. To maintain catalyst stability in flasher 106 and optionally at the base of light ends column 120, carbon monoxide may be introduced from the carbon monoxide recovery unit 150 and/or in line 111 to one or more of the flasher 106, the light ends column 120, or associated conduits. As shown in FIGS. 1 and 2, all or a portion of gaseous stream 110 is directed to carbon monoxide recovery unit 150, which forms carbon monoxide enriched stream 151. As used herein, the term "carbon monoxide enriched stream" means a stream having a carbon monoxide concentration greater than the carbon monoxide concentration of a parent stream from which it is derived. Thus, carbon monoxide enriched stream 151 has a greater concentration of carbon monoxide than gaseous stream 110 and line 111.

Carbonylation product is withdrawn from carbonylation reactor 105 at the thermodynamic conditions described above and at a rate sufficient to maintain a constant level therein and is transmitted to flasher 106 via stream 113. Flasher 106 preferably is maintained at a pressure that is less than reactor 105. In one embodiment, flasher 106 operates at a total pressure of from 0.5 to 10 bar, e.g., from 1 to 5 bar, or 1 to 3 bar. The operating temperature for flasher 106 may range from 50° C. to 150° C., e.g., from 75° C. to 150° C. or from 120° C. to 140° C.

In flasher 106, the carbonylation product is separated in a flash separation step, with or without the addition of heat, to obtain a crude acetic acid stream 115 comprising acetic acid and carbon monoxide, e.g., dissolved and/or entrained carbon monoxide, and a catalyst-containing solution 114, which also may comprise a minor amount of dissolved carbon monoxide. Catalyst-containing solution 114 predominantly contains acetic acid, a metal compound of a carbonylation catalyst, e.g., a metal complex of rhodium and/or iridium, and iodide salt, as well as small quantities of methyl acetate, methyl iodide, water, and possibly corrosion metal contaminants. The corrosion metal contaminants may be removed by passing a portion of the catalyst-containing solution 114 through an exchange resin (not shown), before returning catalyst-containing solution 114 to reactor 105.

Crude acetic acid stream 115 comprises acetic acid, methyl iodide, methyl acetate, water, alkanes, carbon monoxide, other gases, and permanganate reducing compounds (PRC's). At least some, preferably a majority, of the carbon monoxide from recovery unit 107 and/or from carbon monoxide recovery unit 150 that is fed to flasher 106 carries through with crude acetic acid stream 115. In one aspect of the present invention, it is preferred to feed carbon monoxide to the liquid portion in flasher 106 such that the carbon monoxide intimately contacts the catalyst contained therein enhancing catalyst stability, i.e., preventing or reducing catalyst precipitation.

Carbon monoxide may also stabilize entrained catalyst that passes to light ends column 120. As shown in FIG. 1, crude acetic acid stream 115 is directed to purification section 102 and fed to light ends column 120. In one exemplary embodiment, purification section 102 preferably comprises light ends column 120, drying column 130, and vent scrubber 140. Purification section 102 may also comprise a PRC removal system (PRS), additional guard beds and/or a heavy ends column.

Light ends column 120 yields low-boiling overhead vapor stream 122, product side stream 123, and optional bottoms stream 121. Optional bottoms stream 121 may comprise entrained catalyst. Feeding carbon monoxide either to flasher 106 or to the base of light ends column 120 may enhance catalyst stability in the flasher and/or in the base of light ends column and in the optional bottoms stream 121. The temperature at the base of light ends column 120, i.e., temperature of optional bottoms stream 121, preferably is from 120° C. to 170° C. In addition, the temperature at the top of the light ends column, i.e., temperature of low-boiling overhead vapor stream 122, preferably is from 100° C. to 145° C.

Low-boiling overhead vapor stream 122 may comprise methyl iodide, methyl acetate, water, PRC's, acetic acid, alkanes, and dissolved gases. As shown, low-boiling overhead vapor stream 122 preferably is condensed and directed to an overhead phase separation unit 124, which is preferably an overhead decanter. Conditions are desirably maintained such that the condensed low-boiling overhead vapor stream 122, once in decanter 124, will separate into a light phase and a heavy phase. The light phase and heavy phase are withdrawn via lines 125 and 126, respectively. In some embodiments, only a single phase is formed in decanter 125.

Light phase stream 125 preferably comprises water, acetic acid, and PRC's, as well as methyl iodide and methyl acetate. As shown in FIG. 1, at least a portion of light phase stream 125 may be refluxed to light ends column 120. In one embodiment, another portion of light phase stream 125 may also be separated and processed in a PRS (not shown) to remove PRC's. PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof. Suitable PRS's are described in U.S. Pat. Nos. 7,855,306; 7,223,886; and 6,143,930, which are hereby incorporated by reference. Optionally, a portion of light phase stream 125 may also be returned to reaction section 101 via stream 125'. Heavy phase stream 126 from decanter 124 can be conveniently recirculated, either directly or indirectly, to reactor 105.

Product side stream 123 from light ends column 120 comprises acetic acid and water. Product side stream 123 preferably is in the liquid phase and is withdrawn from the light ends column 120 at a temperature from 115° C. to 160° C., e.g., from 125° C. to 155° C. A portion of stream 123 may be returned to light ends column 120 (not shown).

Drying column 130 separates product side stream 123 to yield an overhead stream 131, comprised primarily of water, and a dried product stream 132. The dried purified product stream 132 preferably comprises acetic acid in an amount greater than 90 wt. %, e.g., greater than 95 wt. % or greater than 98 wt. %. The temperature at the base of drying column 130, i.e., temperature of exiting dried purified product stream 132, preferably is from 130° C. to 185° C., e.g., 140° C. to 180° C. or 150° C. to 175° C. The temperature at the top of drying column 130, i.e., temperature of overhead stream 131, preferably is from 110° C. to 150° C., e.g., 120° C. to 150° C. or 130° C. to 145° C. In some embodiments, the pressure in drying column 130 is from 2 bar to 7 bar, e.g., 3 bar to 6 bar, or 4 bar to 5 bar. Optionally, dried purified product stream 132 may be further treated in one or more guard beds (not shown) and/or heavy ends columns (not shown) to further remove impurities, such as halides, or heavier acids, such as propionic acid, and/or esters.

Overhead stream 131 from drying column 130 may be cooled and condensed in overhead receiver 133 to yield a light phase and a heavy phase or optionally a single phase (not shown). A portion of the light phase from receiver 133 may be refluxed to drying column 130 via line 134. The remaining portion of light phase 135 as well as at least a portion of heavy phase 136 may be returned to reaction section 101.

In purification section 102 uncondensed gases, such as carbon monoxide, may be removed by vent stream 127 from decanter 124 and treated in vent scrubber 140. A scrubbing solvent, which is preferably chilled to less than 25° C., may be fed via feed 141 to vent scrubber 140 to scrub vent stream 127. Exemplary scrubbing solvents include methanol, methyl acetate, acetic acid, and mixtures thereof. Vent scrubber 140 removes from vent stream 127 low boiling point components, such as methyl iodide. These low boiling point components exit scrubber 140 via line 142 and optionally may be returned to reaction section 101, e.g., to reactor 105. The overheads of scrubber 140 may exit as gas stream 143 that comprises carbon monoxide and may be directed to carbon monoxide recovery unit 150. Gas stream 143 may comprise less than 75 mol. % carbon monoxide, e.g., less than 65 mol. % or less than 50 mol. %. In one embodiment, gas stream 143 may be compressed prior to being introduced to carbon monoxide recovery unit 150. As a result of the scrubbing, gas stream 143 preferably comprises substantially no halide compounds, such as methyl iodide.

Carbon monoxide recovery unit 150 may include, but is not limited to, pressure swing adsorbers (PSA), vacuum swing adsorbers (VSA), thermal swing adsorbers (TSA), and/or membranes. Membranes may be arranged in an array. Suitable membranes include shell and tube membrane modules having one or more porous material elements therein. Non-porous material elements may also be included. The material elements may include polymeric elements such as polyvinyl alcohol, cellulose esters, and perfluoropolymers. Membranes that may be employed in embodiments of the present invention include those described in Baker, et al., "Membrane separation systems: recent developments and future directions," (1991) pages 151-169, Perry et al., "Perry's Chemical Engineer's Handbook," 7th ed. (1997), pages 22-37 to 22-69, the entireties of which are incorporated herein by reference.

Although one carbon monoxide recovery unit 150 is shown in FIGS. 1 and 2, multiple carbon monoxide recovery units 150 may be used in accordance with embodiments of the present invention. In one embodiment, there may be separate carbon monoxide recovery units for gas stream 112 and gas stream 143.

The gas streams, such as streams 112 and 143, from the reaction section 101 and/or purification section 102, are fed to carbon monoxide recovery unit 150 to derive a carbon monoxide enriched stream 151 and a purge gas stream 152. Carbon monoxide enriched stream 151 preferably comprises at least 85 mol. % carbon monoxide, e.g. at least 90 mol. % and at least 95 mol. %. Although high carbon monoxide purity may be achievable, it may not critical when feeding stream 151 downstream of reactor 105. This may reduce capital and energy requirements of carbon monoxide recovery unit 150. Purge gas stream 152 comprises hydrogen, carbon dioxide, nitrogen and other gaseous components and may be vented to the atmosphere, for example, via a flare, or used as a fuel. Preferably, purge gas stream 152 comprises a low carbon monoxide concentration, e.g., less than 15 mol. % carbon monoxide, or more preferably less than 5 mol. %.

As discussed above, carbon monoxide enriched stream 151 is preferably returned to one or more locations downstream of reactor 105 to stabilize the catalyst and thus reduce catalyst precipitation. At least a portion of carbon monoxide enriched stream 151 may be added to stream 113, which contains carbonylation reaction product as well as carbonylation catalyst. The addition of carbon monoxide from stream 151 may beneficially provide for stabilization of the residual catalyst in line 113. This may inhibit or prevent precipitation of the catalyst when being transmitted from reactor 105 to flasher 106. In addition, stabilizing catalyst in stream 113 with the carbon monoxide in stream 151 may beneficially stabilize the catalyst in flasher 106 since the carbon monoxide from stream 151 will pass through to flasher 106 via line 113. In some embodiments, a portion of the carbon monoxide enriched stream 151 may be fed to line 113 and the remaining portion to the liquid portion in flasher 106, e.g., via optional line 155.

Optionally, carbon monoxide enriched stream 151 may be compressed as necessary when added to stream 113 or elsewhere as appropriate. In one embodiment, carbon monoxide enriched stream 151 may be compressed to a pressure that is substantially equal to or greater than the pressure of the reactor. Preferably, carbon monoxide enriched stream 151 may be added downstream of reactor without further compressing the carbon monoxide enriched stream 151.

In other embodiments, one or more portions of carbon monoxide enriched stream 151 are fed to one or more other locations. Examples include: (1) the base of flasher 106, which may be fed via optional line 155; (2) the base of light ends column 120, which may be fed via optional line 156; (3) reboiler stream 128 of light ends column 120, which may be fed via optional line 157; and (4) catalyst containing solution stream 114, which may be fed via optional line 158. At least a portion of carbon monoxide enriched stream 151 may be fed as necessary to one or more of these locations to enhance catalyst stability.

In an exemplary embodiment, a portion of the carbon monoxide enriched stream 151 may be added to stream 113 and the remaining portion added to catalyst containing solution stream 114 withdrawn from the base of flasher 106. In this aspect, the carbon monoxide may be ultimately returned to reactor 105 and used in the carbonylation reaction to form additional acetic acid. In another exemplary embodiment, a portion of the carbon monoxide enriched stream 151 may be added to stream 113 and the remaining portion added to the base of flasher 106. In still other embodiments, none of the carbon monoxide enriched stream 151 is added to stream 113, and instead the carbon monoxide enriched stream 151 is added, in whole or part, to the base of flasher 106 and/or to the base of the light ends column 120 and/or to the reboiler system 128 of the light ends column.

When carbon monoxide enriched stream 151 is added to carbonylation solution stream 113, flasher 106, light ends column 120, or reboiler stream 128, the carbon monoxide may stabilize the catalyst and may be recycled via vent stream 127 from decanter 124. Preferably, carbon monoxide enriched stream 151 is added to the carbonylation solution stream 113 and/or flasher 106.

In optional embodiments, at least a portion of the carbon monoxide enriched stream 151 may be fed with carbon monoxide feed stream 103 to reactor 105. Additionally, at least a portion of carbon monoxide enriched stream 151 may be added to any pump-around loops (not shown) used for regulating the temperature of reactor 105. It is preferred, however, that a majority of the carbon monoxide enriched stream 151 be fed to the system at locations downstream of reactor 105.

In addition to or as an alternative to sending carbon monoxide enriched stream 151 to a location downstream of the reactor, as described above, a portion of vent stream 127 may be directed to such locations without first being treated in vent scrubber 140 or in carbon monoxide recovery unit 150, as shown by stream 127'. Thus, a portion of vent stream 127 may be compressed as necessary when added to stream 113 or elsewhere as appropriate. In one embodiment, stream 127' may be compressed to a pressure that is substantially equal to or greater than the pressure of the reactor. Preferably, stream 127' may be added downstream of reactor without further compressing the carbon monoxide enriched stream 151. In other embodiments, one or more portions of stream 127' are fed to one or more other locations. Examples include: (1) the base of flasher 106; (2) the base of light ends column 120; (3) reboiler stream 128 of light ends column 120; and (4) catalyst containing solution stream 114. At least a portion of vent stream 127, e.g., stream 127', may be fed as necessary to one or more of these locations to enhance catalyst stability.

The present invention is also applicable to acetic anhydride production systems and acetic acid, acetic anyhydride coproduction systems, such as those described in U.S. Pat. Nos. 5,380,929; 5,922,911; 6,130,355; 6,541,666; and 7,737,298, the entireties of which are incorporated herein by reference. In one embodiment, for example, the invention is to method for enhancing catalyst stability in an acetic acid, acetic anhydride co-production process, comprising the steps of reacting carbon monoxide with at least one reactant selected from the group consisting of methanol, methyl acetate, methyl formate, dimethyl ether and mixtures thereof in a reactor containing a reaction medium to produce a reaction product comprising acetic acid and acetic anhydride; venting a gaseous stream from the reactor; and introducing at least a portion of the vented gaseous stream downstream of the reactor. The flow rate of the vented gaseous stream is optionally as described above, e.g., from 0.1 to 10% of the flow rate of the carbon monoxide fed to the reactor. The portion of the vented gaseous stream optionally is introduced to the reaction product withdrawn from the reactor and/or to one or more vessels employed in the acetic acid/acetic anhydride separation scheme. For example, crude coproduction product is typically sent to a falling film evaporator, which separates product from catalyst for catalyst recovery. The separated product may be sent to a series of distillation columns, typically including a lights column for removing light ends, an acetic acid column for separating acetic acid product (and for subsequent recycle), and an acetic anhydride column for separating acetic anhydride product from heavy ends (tar). The carbon monoxide may be fed to one or more of these various separation units, but preferably is directed to the falling film evaporator.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A method for enhancing catalyst stability in an acetic acid production process comprising the steps of:
    introducing a carbon monoxide stream into a reactor;
    reacting the carbon monoxide with at least one reactant selected from the group consisting of methanol, methyl acetate, methyl formate, dimethyl ether and mixtures thereof in a reactor containing a reaction medium to produce a reaction product comprising acetic acid and unreacted carbon monoxide;
    venting a gaseous reactor vent stream from the reactor;
    separating the reaction product into a crude acetic acid stream and a catalyst-containing solution;
    distilling the crude acetic acid stream to yield a product stream comprising acetic acid and an overhead vapor stream comprising at least a portion of the unreacted carbon monoxide;
    condensing the overhead vapor stream and directing the condensed overhead vapor stream to a decanter;
    withdrawing a gaseous stream comprising carbon monoxide from the decanter; and
    introducing at least a portion of the withdrawn carbon monoxide downstream of the reactor and upstream of the decanter to create a carbon monoxide recycle loop,
    wherein the introducing of at least a portion of the withdrawn carbon monoxide downstream of the reactor provides for an increased carbon monoxide flow rate in the reactor and an increased reactor vent rate, based on a process that does not create the carbon monoxide recycle loop.

2. The method according to claim 1, further comprising recovering a carbon monoxide enriched stream from the gaseous stream, and introducing at least a portion of the carbon monoxide enriched stream downstream of the reactor.

3. The method according to claim 2, wherein the reaction product is separated in a flasher.

4. The method according to claim 2, wherein the portion of the carbon monoxide enriched stream is introduced to the flasher.

5. The method according to claim 2, wherein the crude acetic acid stream is distilled in a light ends distillation column.

6. The method according to claim 5, wherein the portion of the carbon monoxide enriched stream is introduced to the light ends distillation column.

7. The method according to claim 2, wherein the portion of the carbon monoxide enriched stream is introduced to the reaction product withdrawn from the reactor.

8. The method according to claim 2, wherein the carbon monoxide enriched stream comprises at least 50 mol. % carbon monoxide.

9. The method according to claim 2, wherein the carbon monoxide enriched stream comprises at least 85 mol. % carbon monoxide.

10. The method according to claim 2, wherein the carbon monoxide enriched stream is derived from a carbon monoxide recovery unit, wherein the carbon monoxide recovery unit is selected from the group consisting of pressure swing adsorbers, vacuum swing adsorbers, thermal swing adsorbers, membranes, and combinations thereof.

11. The method according to claim 10, further comprising scrubbing the gaseous stream to remove halide compounds.

12. The method according to claim 2, further comprising passing the gaseous stream through one or more membranes to derive the carbon monoxide enriched stream.

13. The method according claim 1, wherein the carbon monoxide in the reactor is maintained at a partial pressure of at least 2 bar.

14. The method according to claim 1, further comprising venting a gaseous vent stream comprising carbon monoxide from the reactor.

15. The method according to claim 14, wherein the flow rate of the gaseous vent stream is from 0.1 to 10% of the flow rate of carbon monoxide fed to the reactor.

16. The method according to claim 14, further comprising mixing a portion of the gaseous vent stream with the gaseous stream.

17. The method according to claim 1, further comprising recovering a purge stream from the gaseous stream, wherein the purge stream comprises less than 15 mol. % carbon monoxide.

18. A method for enhancing catalyst stability in an acetic acid production process comprising the steps of:
introducing a carbon monoxide stream into a reactor;
reacting the carbon monoxide with at least one reactant selected from the group consisting of methanol, methyl acetate, methyl formate, dimethyl ether and mixtures thereof in a reactor containing a reaction medium to produce a reaction product comprising acetic acid;
venting a gaseous reactor vent stream from the reactor;
recovering a first carbon monoxide enriched stream from the vented gaseous stream;
separating the reaction product into a crude product stream comprising acetic acid and a catalyst-containing solution;
distilling the crude product stream to yield an acetic acid stream and an overhead vapor stream comprising unreacted carbon monoxide;
condensing the overhead vapor stream and directing the condensed overhead vapor stream to a decanter;
withdrawing uncondensed gases from the decanter;
recovering a second carbon monoxide enriched stream from the uncondensed gases; and
introducing at least a portion of the first carbon monoxide enriched stream and at least a portion of the second carbon monoxide enriched stream downstream of the reactor and upstream of the decanter to create a carbon monoxide recycle loop,
wherein the introducing of at least a portion of the withdrawn carbon monoxide downstream of the reactor provides for an increased carbon monoxide flow rate in the reactor and an increased reactor vent rate, based on a process that does not create the carbon monoxide recycle loop.

19. The method according to claim 18, wherein the flow rate of the vented gaseous stream comprises from 0.1 to 10% of the flow rate of the carbon monoxide fed to the reactor.

20. The method according to claim 18, wherein the portion of the first carbon monoxide enriched stream is introduced to the reaction product withdrawn from the reactor.

21. The method according to claim 18, wherein the reaction product is separated in a flasher and the portion of the second carbon monoxide enriched stream is introduced to the flasher.

22. A method for enhancing catalyst stability in an acetic acid production process comprising the steps of:
introducing a carbon monoxide stream into a reactor;
reacting the carbon monoxide with at least one reactant selected from the group consisting of methanol, methyl acetate, methyl formate, dimethyl ether and mixtures thereof in a reactor containing a reaction medium to produce a reaction product comprising acetic acid;
venting a gaseous reactor vent stream from the reactor;
separating the reaction product into a crude acetic acid stream and a catalyst-containing solution;
distilling the crude acetic acid stream to yield a product stream comprising acetic acid and an overhead stream comprising unreacted carbon monoxide;
separating a carbon monoxide enriched stream from the overhead stream; and
introducing at least a portion of the carbon monoxide enriched stream downstream of the reactor and upstream of the decanter to create a carbon monoxide recycle loop,
wherein the introducing of at least a portion of the withdrawn carbon monoxide downstream of the reactor provides for an increased carbon monoxide flow rate in the reactor and an increased reactor vent rate, based on a process that does not create the carbon monoxide recycle loop.

23. The method of claim 1, wherein the introducing is performed without further compressing the at least a portion of the withdrawn carbon monoxide.

24. The method of claim 18, wherein the introducing is performed without further compressing the at least a portion of the withdrawn carbon monoxide.

25. The method of claim 22, wherein the introducing is performed without further compressing the at least a portion of the withdrawn carbon monoxide.

* * * * *